(12) United States Patent
Sekiguchi et al.

(10) Patent No.: US 8,124,315 B2
(45) Date of Patent: *Feb. 28, 2012

(54) OPTICAL RECORDING MEDIUM

(75) Inventors: Hiroyoshi Sekiguchi, Yokohama (JP); Kazunori Ito, Yokohama (JP); Hiroshi Deguchi, Yokohama (JP); Hiroko Ohkura, Yokohama (JP); Masaki Kato, Sagamihara (JP); Mikiko Takada, Yokohama (JP)

(73) Assignee: Ricoh Company, Ltd., Tokyo (JP)

( * ) Notice: Subject to any disclaimer, the term of this patent is extended or adjusted under 35 U.S.C. 154(b) by 1124 days.

This patent is subject to a terminal disclaimer.

(21) Appl. No.: 11/662,219

(22) PCT Filed: Sep. 7, 2005

(86) PCT No.: PCT/JP2005/016862
§ 371 (c)(1),
(2), (4) Date: Sep. 21, 2007

(87) PCT Pub. No.: WO2006/028251
PCT Pub. Date: Mar. 16, 2006

(65) Prior Publication Data
US 2008/0050673 A1 Feb. 28, 2008

(30) Foreign Application Priority Data

Sep. 9, 2004 (JP) ................. 2004-261830
Sep. 13, 2004 (JP) ................. 2004-265778

(51) Int. Cl.
*G11B 7/24* (2006.01)
(52) U.S. Cl. .................. 430/270.13
(58) Field of Classification Search .......... None
See application file for complete search history.

(56) References Cited

U.S. PATENT DOCUMENTS

| | | | |
|---|---|---|---|
| 6,149,999 A | 11/2000 | Suzuki et al. | |
| 6,827,999 B2 * | 12/2004 | Ito et al. | 428/64.1 |
| 6,958,180 B2 * | 10/2005 | Hibino et al. | 428/64.1 |
| 7,485,357 B2 * | 2/2009 | Takada et al. | 428/64.4 |
| 2002/0054983 A1 | 5/2002 | Nishihara et al. | |
| 2003/0012917 A1 | 1/2003 | Harigaya et al. | |
| 2003/0214857 A1 * | 11/2003 | Horie et al. | 365/200 |
| 2004/0105952 A1 * | 6/2004 | Deguchi et al. | 428/64.4 |
| 2004/0115386 A1 * | 6/2004 | Shinkai et al. | 428/64.1 |
| 2004/0141447 A1 | 7/2004 | Yuzurihara et al. | |
| 2004/0248036 A1 | 12/2004 | Ohno et al. | |
| 2006/0077884 A1 | 4/2006 | Ohkura et al. | |
| 2006/0246270 A1 | 11/2006 | Takada et al. | |

FOREIGN PATENT DOCUMENTS

| | | |
|---|---|---|
| EP | 0887791 A1 | 12/1998 |
| EP | 1187119 A2 | 3/2002 |
| EP | 1690693 A1 | 8/2006 |
| EP | 1712367 A1 | 10/2006 |
| EP | 1787293 B1 | 3/2010 |
| JP | 11-39709 | 2/1999 |
| JP | 2000-76702 | 3/2000 |
| JP | 2001-39031 | 2/2001 |
| JP | 2002-225437 | 8/2002 |
| JP | 2002-264514 | 9/2002 |
| JP | 2003-248967 | 9/2003 |
| JP | 2003-291534 | 10/2003 |
| JP | 2003-305955 | 10/2003 |
| JP | 3494044 | 11/2003 |
| JP | 2004-174868 | 6/2004 |
| JP | 2004-185794 | 7/2004 |
| JP | 2004-199784 | 7/2004 |
| JP | 2004-206851 | 7/2004 |
| JP | 2004-227743 | 8/2004 |
| JP | 2004-322630 | 11/2004 |
| TW | 200527421 | 8/2005 |
| WO | WO 2005/051672 | * 9/2005 |

OTHER PUBLICATIONS

Sep. 15, 2009 Japanese official action in connection with a counterpart Japanese patent application No. 2004-265778.
Aug. 24, 2010 Indian examination report in connection with counterpart Indian patent application.
European search report in connection with a counterpart European patent application No. 05 78 3408, Dec. 20, 2005.
Taiwanese official action (and English translation thereof) in connection with a counterpart Taiwanese patent application No. 94131165.

* cited by examiner

*Primary Examiner* — Cynthia H Kelly
*Assistant Examiner* — Anna Verderame
(74) *Attorney, Agent, or Firm* — Cooper & Dunham, LLP (57) ABSTRACT

An optical recording medium contains a recording layer being composed of a phase-change recording material where at least four elements, Ga, Sb, Sn and Ge are contained and the transfer linear velocity is 20 m/s to 30 m/s, and when the wavelength of a recording/reproducing light is within the range of 650 nm to 665 nm and the recording linear velocity is 20 m/s to 28 m/s, the refractive index Nc and the extinction coefficient Kc in a crystalline state and the refractive index Na and the extinction coefficient Ka in an amorphous state in the recording layer respectively satisfy the following numerical expressions: $2.0 \leq Nc \leq 3.0$, $4.0 \leq Kc \leq 5.0$, $4.0 \leq Na \leq 5.0$, and $2.5 \leq Ka \leq 3.1$, and information is recordable at the range of 20 m/s to 28 m/s of recording linear velocity.

13 Claims, 7 Drawing Sheets

OPTICAL RECORDING MEDIUM

TECHNICAL FIELD

The present invention relates to a phase-change optical recording medium (such as, DVD-RW, DVD+RW or DVD-RAM) where the irradiation of laser beam causes optical changes to a recording material of a recording layer therefore information is recorded and reproduced; and the information is rewritable, and relates specifically to an optical recording medium having performance responsive to high-speed recording linear velocity, as well.

BACKGROUND ART

Conventionally, in a phase-change optical recording medium where information is recorded and reproduced onto/from a recording layer and the information is rewritable, the recording layer contains four elements, Ag, In, Sb and Te, as primary components. The objective is to improve the recording linear velocity on the basis of stable signal processing, making it possible to stably perform recording and reproducing at 1x-speed to 4x-speed of a recording linear velocity of DVD-ROM (3.49 m/s), which is now commercially available.

In the optical recording medium, the manner in which to conduct heat subtly changes depending upon an optical constant or film thickness of each layer laminated on a substrate, and may greatly affect the recording characteristic in a mark recorded on the recording layer, or reflectance or modulation factor may change. As in Patent Literature 1, the film thickness of each layer laminated onto a substrate, an optical constant of a crystalline phase and an amorphous phase in the recording layer, an optical constant regarding a protective layer and a reflective layer, and the condition for groove depth of a transparent substrate are important factors relating to recording characteristics and signal processing.

In addition, in order to realize high-speed recording, recording must be performed with additionally higher power, so the storage reliability becomes more severe than in comparison with the conventional art. Using Ag having high thermal conductivity for a reflective layer binds with S in ZnS—$SiO_2$ of a protective layer and $Ag_2S$ is formed, so it is necessary to establish a sulfidation prevention layer between the reflective layer and the protective layer. However, recording with higher power causes the easy occurrence of peeling-off with interference between the Ag reflective layer and the sulfidation prevention layer, leading to the problem that a disc defect easily occurs after repeated recording or after long-term storage in a severe environment.

As a related well-known technology, Patent Literature 2 discloses an invention where tantalum oxide, tantalum and nickel are used for an intermediate layer making contact with an Ag reflective layer, and $M_w(Sb_zTe_{1-z})_{1-w}$, provided that $0 \leq w \leq 0.3$ and $0.5 \leq z \leq 0.9$, for a recording layer. However, the invention has different constituent elements from those in the sulfidation prevention layer of the present invention; and in addition, recording is performed at 2x-speed of CD (2.4 m/s), which is at a lower velocity, and lower density compared to those in the present invention.

Further, Patent Literature 3 relating to the present application by the applicant discloses an invention where Si, SiC, Ge and GeCr are used for a sulfidation prevention layer making contact with an Ag reflective layer, and $Ga\alpha Ge\beta In\gamma Sb\delta Te\epsilon$ (provided that $0<\alpha<7$, $0<\beta<10$, $0<\gamma<5$, $60<\delta<80$ and $0<\epsilon<5$) is used for a recording layer. However, the invention has different constituent elements from those in the sulfidation prevention layer of the present invention. In addition, recording is performed at 20 m/s at maximum, which is at a lower velocity compared to that of the present invention.

Further, Patent Literature 4 discloses an invention where a recording layer composed of GeSbIn, and recording is performed at 2.4 m/s to 9.6 m/s, which is at a lower velocity compared to that in the present invention.

The present invention is directed at providing a DVD+RW recordable at 6x-speed to 8x-speed of DVD-ROM (hereafter, simply referred to as '6x-speed to 8x-speed), and optical constants in a crystalline state and an amorphous state in a recording layer, and the groove condition to control high reflectance are studied; concurrently, the sulfidation prevention layer is also studied.

Patent Literature 1: Japanese Patent Application Laid-Open (JP-A) No. 2000-76702
Patent Literature 2: Japanese Patent (JP-B) No. 3494044
Patent Literature 3: Japanese Patent Application Laid-Open (JP-A) No. 2003-248967
Patent Literature 4: Japanese Patent Application Laid-Open (JP-A) No. 2001-39031

SUMMARY

In an aspect of this disclosure, there is provided a DVD+RW medium repeatedly recordable at a high linear velocity, 20 m/s to 28 m/s (approximately 6x-speed to 8x-speed), and where recording characteristic and storage characteristic are also excellent. In another aspect, there is provided a DVD+RW medium where the reflectance of the recording layer is appropriately reduced. In another aspect, there is provided a phase-change optical recording medium where it becomes difficult for disc defects to occur due to loose film to occur even after repeated recording or long-term storage in a severe environment by the improvement of adhesion between the reflective layer and the sulfidation prevention layer.

Other aspects are described herein, such as, for example, the following.

1) An optical recording medium comprising: a transparent substrate, a first protective layer disposed on the transparent substrate, a recording layer disposed on the first protective layer, a second protective layer disposed on the recording layer, and a reflective layer disposed on the second protective layer, wherein the recording layer is composed of a phase-change recording material comprising Ga, Sb, Sn and Ge, and where the transfer linear velocity is 20 m/s to 30 m/s, wherein when the wavelength of a recording and reproducing light is within the range of 650 nm to 665 nm and the recording linear velocity is 20 m/s to 28 m/s, the refractive index Nc and the extinction coefficient Kc in a crystalline state and the refractive index Na and the extinction coefficient Ka in an amorphous state in the recording layer respectively satisfy the following numerical expressions: $2.0 \leq Nc \leq 3.0$, $4.0 \leq Kc \leq 5.0$, $4.0 \leq Na \leq 5.0$, and $2.5 \leq Ka \leq 3.1$, and wherein information is recordable at the range of 20 m/s to 28 m/s of recording linear velocity.

2) The optical recording medium according to 1), wherein when the mutual composition ratios (atomic %) of the four elements, Ga, Sb, Sn and Ge, in the recording layer are regarded as $\alpha$, $\beta$, $\gamma$ and $\delta$, respectively, these satisfy the following numerical expressions: $2 \leq \alpha \leq 11$, $59 \leq \beta \leq 70$, $17 \leq \gamma \leq 26$, $2 \leq \delta \leq 12$, $84 \leq \beta+\gamma \leq 88$, and $\alpha+\beta+\gamma+\delta=100$.

3) The optical recording medium according to 2), wherein the total of contents of the four elements, Ga, Sb, Sn and Ge, in the recording layer is 95 atomic % or greater relative to all elements in the recording layer.

4) The optical recording medium according to 3), wherein the recording layer further comprises Te.

5) The optical recording medium according to any of 1) to 4), wherein the film thickness of the first protective layer is 30 nm to 100 nm, the film thickness of the recording layer is 5 nm to 50 nm, the film thickness of the second protective layer is 3 nm to 15 nm and the film thickness of the reflective layer is 100 nm to 300 nm.

6) The optical recording medium according to any of 1) to 5), wherein the transparent substrate has a wobbled groove with 0.74±0.03 μm of track pitch, 22 nm to 40 nm of groove depth and 0.2 μm to 0.3 μm of groove width.

7) The optical recording medium according to any of 1) to 6), wherein the optical recording medium further comprises a sulfidation prevention layer between the second protective layer and the reflective layer; and the first protective layer and the second protective layer comprises a mixture of ZnS and $SiO_2$, respectively, the sulfidation prevention layer comprises a mixture of TiC and TiO, and the reflective layer comprises Ag or an alloy where Ag is a main component.

8) The optical recording medium according to 7), wherein the total film thickness of the second protective layer and the sulfidation prevention layer is 7 nm to 20 nm.

9) The optical recording medium according to 8), wherein the total film thickness of the second protective layer and the sulfidation prevention layer is 7 nm to 15 nm.

10) The optical recording medium according to any of 7) to 9), wherein the composition of the sulfidation prevention layer is $(TiC)_p(TiO)_{100-p}$, wherein 'p' represent percentage by mass and satisfy the following numerical expressions, $50 \leq p \leq 80$.

11) The optical recording medium according to any of 7) to 10), wherein the optical recording medium further comprises a layer containing a mixture of $ZrO_2$, $Y_2O_3$, and $TiO_2$ with 2 nm to 8 nm of film thickness between the second protective layer and the sulfidation prevention layer.

12) The optical recording medium according to any of 7) to 11), wherein the optical recording medium further comprises a layer containing $SiO_2$ with 2 nm to 4 nm of film thickness between the first protective layer and the phase-change recording layer.

BRIEF DESCRIPTION OF DRAWINGS

FIG. 7 is a chart showing the comparison result of reflectance at an unrecorded part in Examples A-3, A-24 and A-25.

BEST MODE FOR CARRYING OUT THE INVENTION

The present invention is described hereafter.

In the optical recording medium of the present invention, a first protective layer; a recording layer composed of a phase-change recording material comprising at least four elements, Ga, Sb, Sn and Ge, and where a transfer linear velocity is 20 mg/s or faster; a second layer; and a reflective layer are laminated onto a transparent substrate in this order. The transfer linear velocity is a physical quantity substituting a crystallization kinetic unique to each phase-change recording material, and herein, it indicates a velocity where the reflectance starts decreasing rapidly in the case of researching the scanning speed dependency of crystalline reflectance by irradiating a continuous light with 18 mW. If a phase-change recording material where the transfer linear velocity is 20 m/s or faster is used, no amorphousness is occurred even though a light is continuously irradiated while the optical recording medium is rotated at less than 20 m/s. Further, if a phase-change recording material where the transfer linear speed is 30 m/s or slower is used, the amorphousness can be easily conducted at approximately 6x-speed to 8x-speed of the recording linear velocity. If the transfer linear velocity becomes faster than this, the amorphousness becomes difficult and recording becomes difficult.

As a recording material of the recording layer, a phase-change recording material responsive to the recording linear velocity at approximately 6x-speed to 8x-speed is required.

In the present invention, it is essential to record an amorphous mark more securely than the case of recording the mark at 1x-speed to 4x-speed, and for the absorption coefficient in the crystalline state of the recording layer, the higher the better. However, if it is excessively high, the remaining heat is filled and characteristic deteriorates. Further, for the refractive index in the amorphous state, the greater the better. There is a report that it is desirable that the refractive index & the extinction coefficient in the crystalline state and the refractive index & the extinction coefficient in the amorphous state in the AgInSbTe-base phase-change recording material, which is a conventional phase-change recording material, are within the range of 2 to 4, 2 to 4, 2.5 to 4 and 2.5 to 3.5, respectively (Patent Literature 1). As result of researching the GaSbSnGe-base phase-change recording material with reference to these findings by the inventors of the present application, the result shown in the below-described Table 1 was obtained. Furthermore, "as-depo optical constant" in the table is equivalent to the optical constant in the amorphous state.

On the basis of the results in Table 1, in the present invention, when the wavelength of recording/reproducing light is within the range of 650 nm to 665 nm and the recording linear speed is 20 m/s to 28 m/s (approximately 6x-speed to 8x-speed), a phase-change recording material where the refractive index Nc & the extinction coefficient Kc in the crystalline state and the refractive index Na & the extinction coefficient Ka in the amorphous state in the recording layer are within the following ranges is used:

$2.0 \leq Nc \leq 3.0$ $4.0 \leq Kc \leq 5.0$ $4.0 \leq Na \leq 5.0$ $2.5 \leq Ka \leq 3.1$ Furthermore, when the wavelength of the recording/reproducing light is within the range of 650 nm to 665 nm and the recording linear velocity is 20 m/s to 28 m/s (approximately 6×-speed to 8×-speed), the refractive index Nc & the extinction coefficient Kc in the crystalline state and the refractive index Na & the extinction coefficient Ka in the amorphous state in the recording layer can be measured as follows. Immediately after the preparation of the recording layer composed of the phase-change recording layer with 100 nm of thickness on a polycarbonate transparent substrate with 0.6 mm of thickness, Na and Ka in the amorphous state in the recording layer are measured by spectroellipsometry. Furthermore, after the initialization of the phase-change recording layer with an initializer, Na and Ka in the crystalline phase are measured by spectroellipsometry. The optical constants are measured by spectroellipsometry with a VASE and a WVASE32 software (J.A. Woollam Japan Co., Inc.). The initializer used here is a POP120-7AH (Hitachi Computer Peripherals Co., Ltd.). The conditions for the initialization are 900 mW of laser power, 11 m/s of linear velocity, and 37 μm of head feed.

Further, an element(s) other than the four elements, Ga, Sb, Sn and Ge, such as, Te, can be added to the optical recording medium of the present invention. For the added quantity of the element (atomic %), as long as the range is small to some extent, an effect on the above-mentioned refractive index and extinction coefficient is small, and the recording characteristic at high-speed recording, approximately at 6×-speed to 8×-speed, becomes excellent. The below-mentioned Table 2 shows the data in the case that the added element is Te, and it is clear that it is preferable to control the composition ratio at 5 atomic % or less. Preferably the total of contents of the four elements, Ga, Sb, Sn and Ge, in the recording layer is 95 atomic % or greater relative to all elements in the recording layer. Te contributes to the easiness of the initial crystallization. In addition, for the purpose of the improvement of various characteristics, other element, such as In, Zn, Ag or Cu, can be added.

Further, the conventional AgInSbTe-base phase-change recording material is not suitable for high linear velocity recording because the crystallization kinetic is slow, so the amorphous mark cannot be accurately recorded at 6×-speed to 8×-speed. Therefore, the development of a new phase-change recording material recordable at 6×-speed to 8×-speed is required. Up to the present, as a recording material, a three-element material, Ga, Sb and Sn, and the four-element material, Ga, Sb, Sn and Ge, have been developed. However, any material sufficiently responsive to recording at 6×-speed to 8×-speed has not been obtained yet. Then, the inventors of the present application have developed the phase-change recording material responsive to recording at approximately 6×-speed to 8×-speed by determining the composition ratio of each element within the range of several %.

In other words, according to the research up to the present, it has been clear that because the crystallization kinetic of the SbSn compound is very fast, there is a possibility of realizing a high-speed recording medium with excellent recording sensitivity. However, the storage condition at room temperature is poor, so the SbSn compound cannot be independently used as a recording material. Then, if Ga or Ge is added, the amorphousness becomes easier and it results in easy recording. Ga and Ge have a function to slow the crystallization kinetic down, so the crystallization kinetic can be controlled to be responsive to the recording linear velocity at approximately 6×-speed to 8×-speed.

Therefore, in the recording layer of the present invention, it is desirable to satisfy the following conditions regarding the composition ratio (atomic %) of the four elements, Ga, Sb, Sn and Ge, as $\alpha$, $\beta$, $\gamma$ and $\delta$, respectively.

$2 \leq \alpha \leq 11$ $59 \leq \beta \leq 70$ $17 \leq \gamma \leq 26$ $2 \leq \delta \leq 12$ $84 \leq \beta+\gamma \leq 88$ $\alpha+\beta+\gamma+\delta=100$ In the above-mentioned conditions, if Sb is less than 59%, the melting point becomes higher, so the sensitivity becomes poor, and if Sb exceeds 70%, it becomes difficult to record an amorphous mark; thus excellent recording characteristics cannot be obtained. If Sn is less than 17%, the crystallization kinetic starts slowing down, so the sensitivity becomes poor, and if Sn exceeds 26%, the crystallization kinetic becomes excessively fast and it becomes difficult to become amorphous, so it is not preferable. If Ga or Ge is less than 2%, the storage reliability deteriorates, and if Ga exceeds 11% or Ge exceeds 12%, the crystallization temperature becomes excessively high and the initial crystallization becomes difficult, so it is not preferable.

Figure 8:
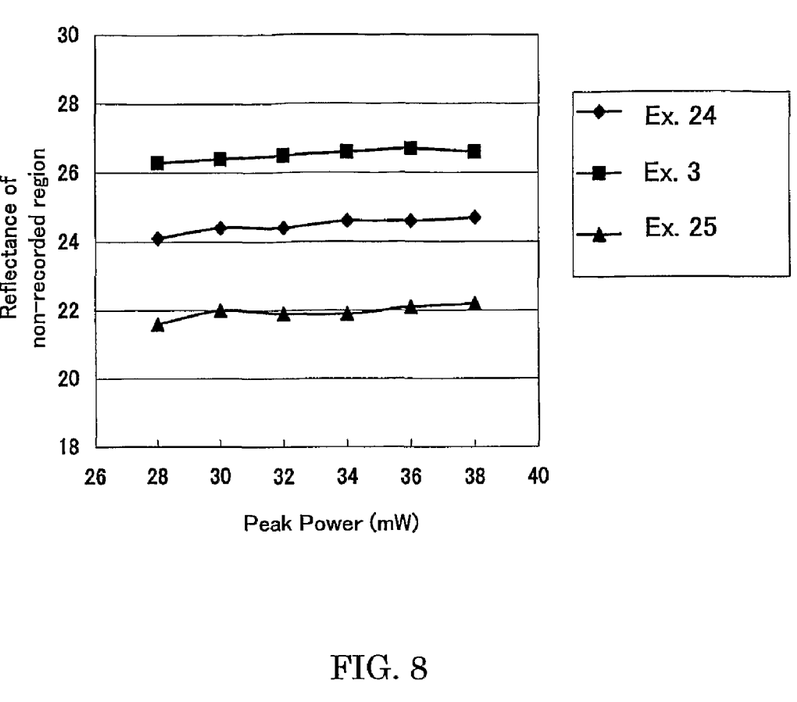
FIG. 8 is a chart showing the experimental result of composition dependency of Sb+Sn in the recording characteristic of GaSbSnGe-base material at 8x-speed.

In addition, if a total of Sb and Sn is less than 84% or exceeds 88%, it causes excessively slow or fast crystallization kinetic, respectively, so a recording layer suitable for recording at 6×-speed to 8×-speed cannot be obtained. Examining the range of the total composition ratio of Sb to Sn where the recording characteristic at 8×-speed becomes excellent, as shown in FIG. 8, the recording characteristic becomes excellent when the total of Sb+Sn is within the range of 84% to 88%, and it has become clear that if the total is out of this range, the recording characteristic deteriorates. As described above, in order to securely perform the high-speed recording, not only providing the composition ratio of Sb to Sn independently, but it is also important to provide the range of the total composition ratio of Sb to Sn.

Figure 1:
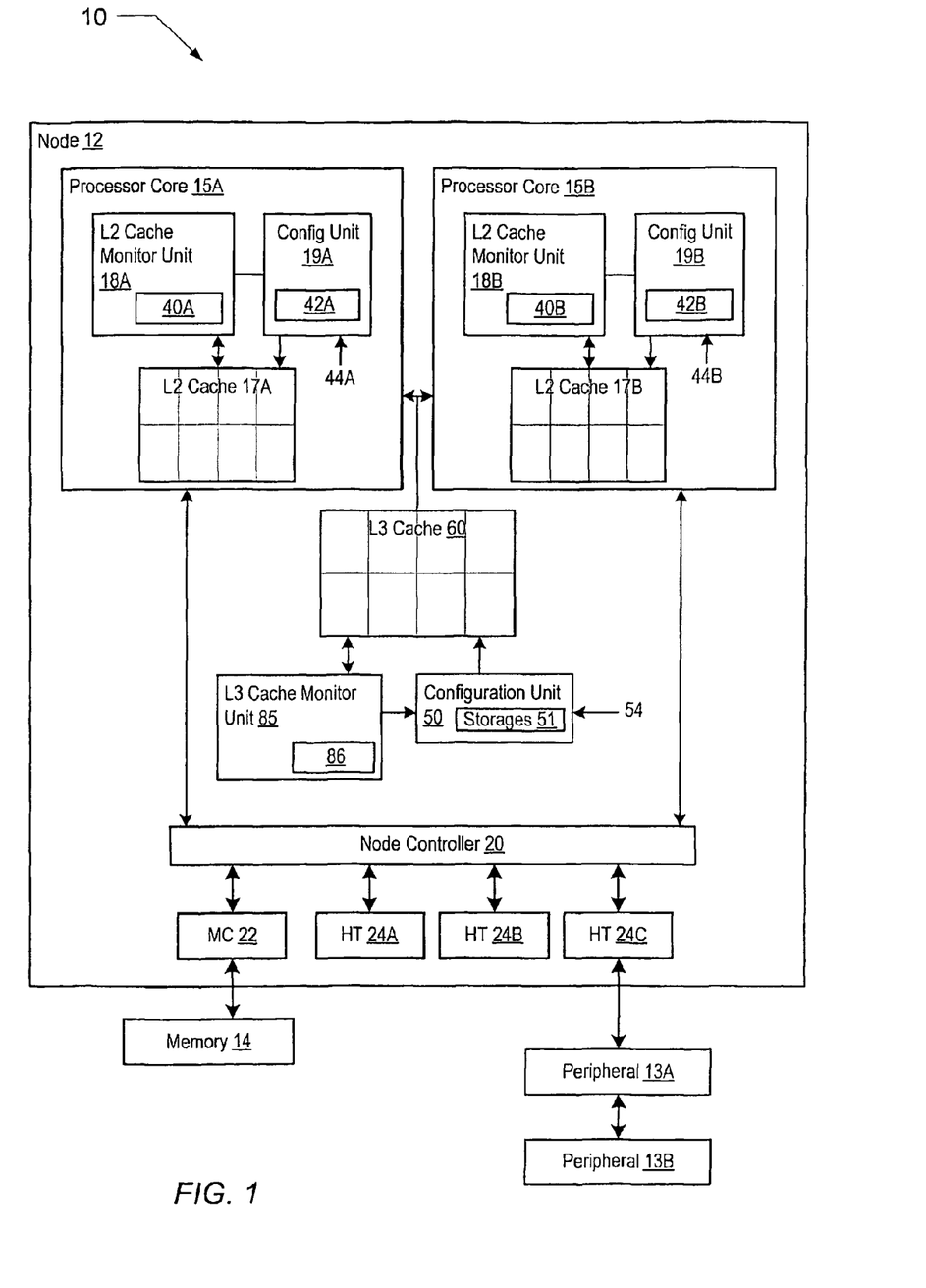
FIG. 1 is a chart showing the comparison result of storage stability of reflectance after the initialization of recording materials $Ga_5Sb_{70}Sn_{17}Ge_8$ and $Ga_{11.9}Sb_{73.1}Sn_{15.0}$.

FIG. 1 shows comparison data of the storage stability according to whether or not Ge is contained. As an example, in $Ga_{11.9}Sb_{73.1}Sn_{15}$ (a line through the diamond points in the chart), which is phase-change recording material containing no Ge, the reflectance after the initialization decreases by 5.7% after 100 hours under the atmosphere at 85% of humidity and 80° C. of temperature, so the crystal condition is changed and recording becomes difficult. Further, even after recording, the storage condition at a space region deteriorates and the jitter characteristic deteriorates. However, in $Ga_5Sb_{70}Sn_{17}Ge_8$ (a line through the square points in the chart), which is a phase-change recording material where Ge is added, the fluctuation is defused, so the reflectance after the initialization decreased by less than 1.5% even after 900 hours.

Figure 2:
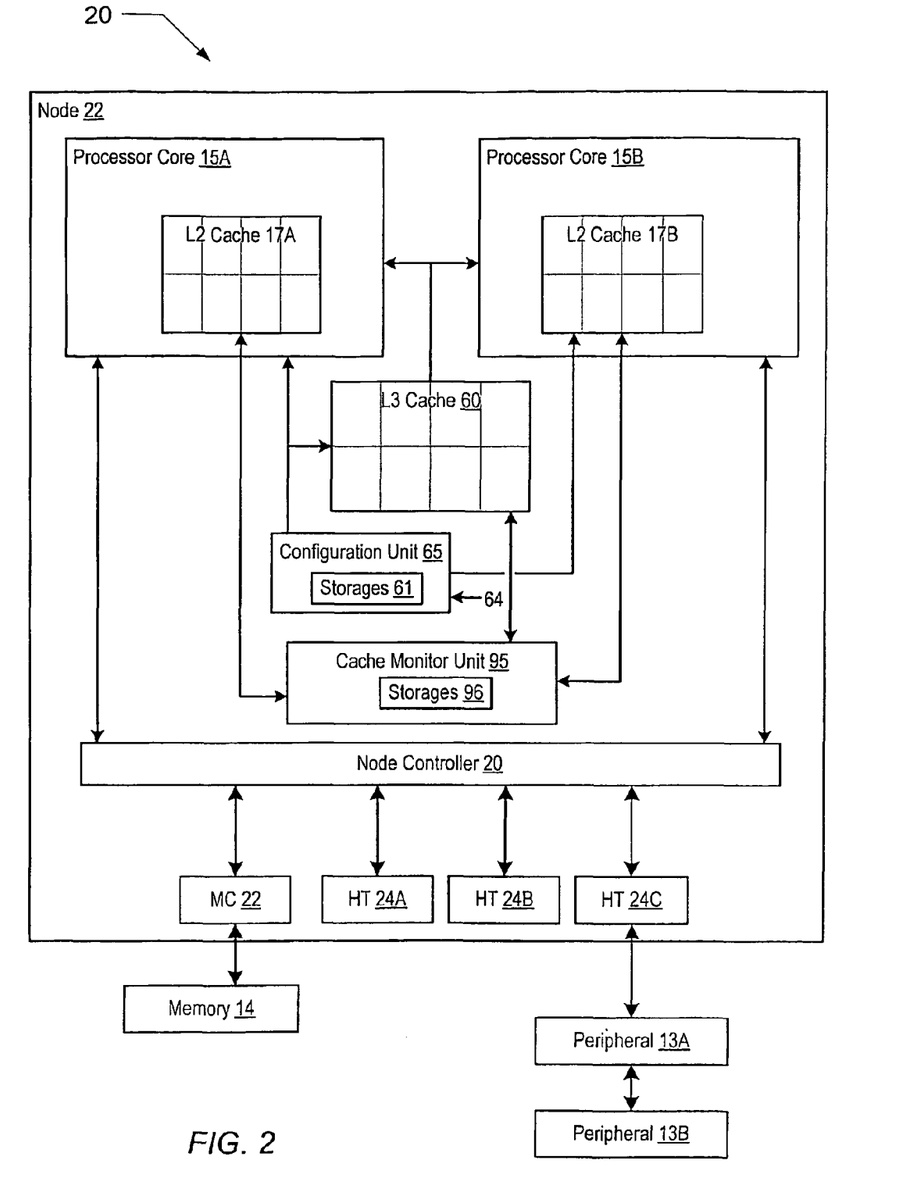
FIG. 2 is a chart showing the storage characteristic of recording medium having recording material of $Ga_5Sb_{70}Sn_{17}Ge_8$, which shows jitter characteristic after initial recording and overwriting.

FIG. 2 shows the storage characteristic of the GaSbSnGe-base phase-change recording material (jitter characteristic after 0 time, 10 times, 1000 times of overwriting (DOW0 (the line through the diamond points in the chart), DOW10 (the line through the square points in the chart) and DOW1000 (the line through the triangular points in the chart), respectively), and no jitter fluctuation occurs even after 900-hour storage.

For the film thickness of the recording layer, the range of 5 nm to 50 nm is desirable, and the range of 10 nm to 20 nm is more preferable. If the film thickness is thinner than 5 nm, defects caused by deterioration due to the repeated recording occur. Further, if the film thickness is thicker than 50 nm, jitter characteristics become poor.

As the first protective layer material, transparent material where a light is efficiently transmitted through and the melting point is 1000° C. or higher is preferable. The oxide, nitride or sulfide is mainly used; among these, it is preferable to use a mixture of ZnS and $SiO_2$ where the internal stress and the absorbency index are small. Since ZnS has small thermal conductivity, the thermal diffusion during recording can be reduced, resulting in the increased recording sensitivity. However, ZnS changes to a crystal at the time of initialization or recording, deteriorating the stability of the recording layer, so a mixture with $SiO_2$ inhibiting the crystallization of ZnS should be used. For the composition, it is preferable that ZnS $SiO_2$=60:40 to 90:10 (mol %). In particular, it is preferable that ZnS $SiO_2$=80:20 (mole ratio).

For the film thickness, the range of 30 nm to 100 nm is desirable. If the film thickness is out of this range, it becomes difficult to certainly secure 60% or greater modulation factor. Further, if the film thickness becomes smaller than 30 nm, because the reflectance fluctuation according to the film thickness becomes greater, it becomes difficult to stably form the layer, and, if the film thickness becomes thicker than 100 nm, the deposition time becomes longer and the productivity of the optical recording medium decreases.

As a second protective layer material, material having the same characteristics as that of the first protective layer is preferable.

For the film thickness, the range of 3 nm to 15 nm is preferable. If the film thickness is less than 3 nm, defects, such as poor recording sensitivity or the reduction of modulation factor, may be encountered. If the film thickness is larger than 15 nm, there is excessive heat, and an amorphous mark becomes smaller due to the residual heat and the recording characteristic becomes poor.

Metal material is used for the reflective layer, and metal material, such as Al, Ag, Au or Cu, or an alloy material of these metal materials, is often used.

For the film thickness, the range of 100 nm to 300 nm is preferable. If the film thickness is less than 100 nm, heat radiation efficiency may be deteriorated. Furthermore, even if the film thickness is larger than 300 nm, the heat radiation efficiency will not be improved, but rather the thickness of the film become larger beyond necessity.

In the aspect where the first protective layer and the second protective layer comprise a mixture of ZnS and $SiO_2$ and the reflective layer comprise Ag or alloy where Ag is a main component, it is preferable to additionally establish a sulfidation prevention layer between the second protective layer and the reflective layer.

Figure 3:
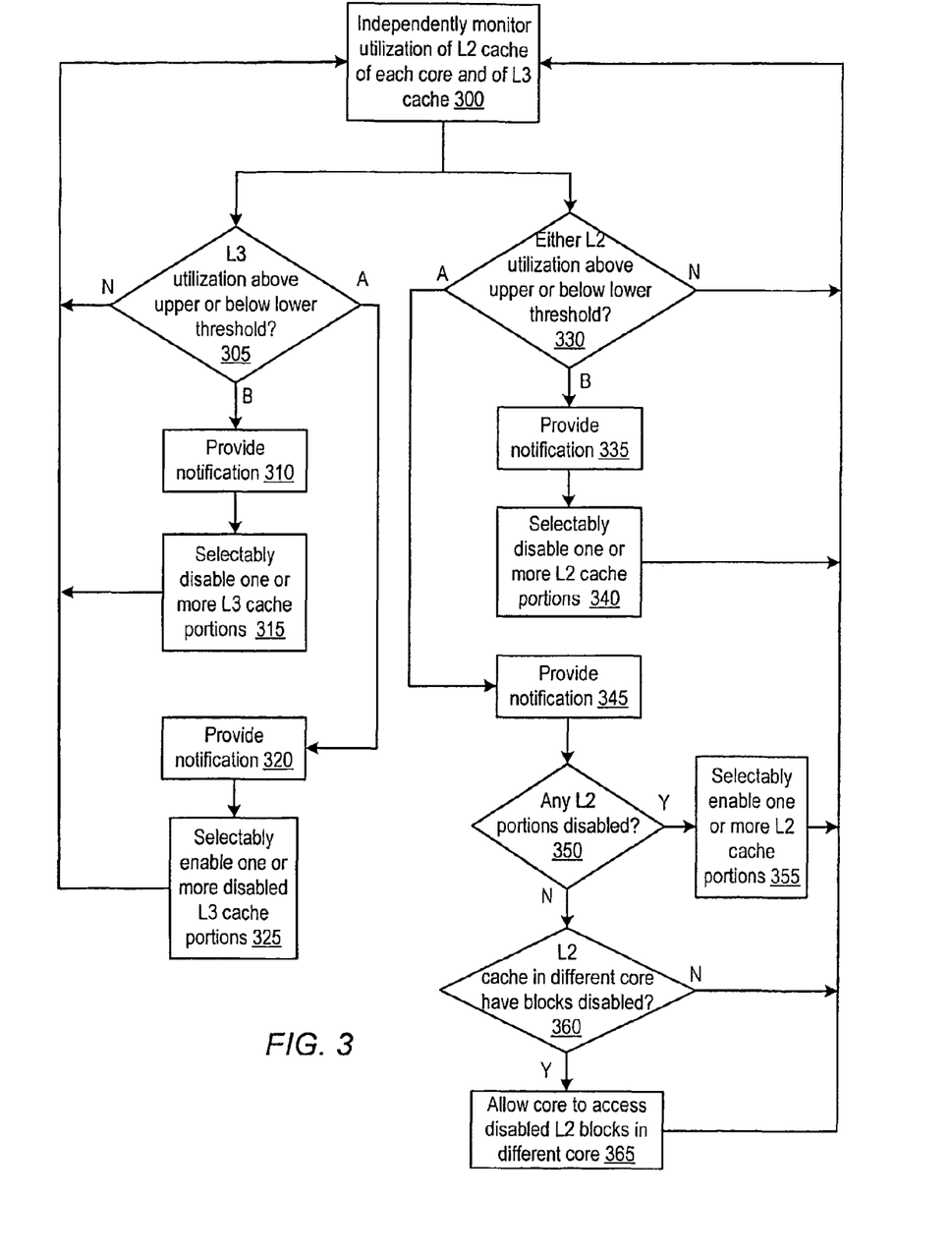
FIG. 3 is a diagram showing a layer construction example of the optical recording medium of the present invention.

FIG. 3 shows a layer construction example of the optical recording medium of the present invention, and is a construction where a first protective layer 2 containing the mixture of ZnS and $SiO_2$, a recording layer 3, a second protective layer 4 containing the mixture of ZnS and $SiO_2$, a sulfidation prevention layer 5 and a reflective layer 6 composed of Ag alloy are laminated in order onto a transparent substrate 1.

A reversible phase transition between the crystal and amorphous states of the phase-change recording layer by the irradiation of a laser beam from the substrate side results in recording and erasure of information. DVD+RW is in the crystalline state before recording, and the irradiation of a modulated laser beam and quenching of the recording layer result in the formation of an amorphous mark. At this time, in order to directly perform the repeated recording of the amorphous mark, it is necessary to crystallize the amorphous mark in shorter period as recording speed increases; therefore, a phase-change recording material with fast crystallization kinetic is required. Further, if using a material with fast crystallization kinetic, re-crystallization progresses from the periphery of the amorphous mark immediately after the mark formation and the mark becomes smaller. In order to reduce the re-crystallization region, it is better to have a quenching structure where cooling velocity is fast, so it is preferable to use Ag or alloy where Ag is a main component, which has high thermal conductivity, for the reflective layer. Herein, the main component means contains 90 atomic % of Ag. Further, as an element forming alloy with Ag; Cu, Pd, Ti, Cr and Ta are provided.

However, Ag tends to migrate rapidly within a layer, and, in addition, it reacts with S to easily form $Ag_2S$. Consequently, it is preferable to establish a sulfidation prevention layer. For the sulfidation prevention layer, SiC or Si, which has been conventionally used, can be used. However, from viewpoints to improve the adhesion between the reflective layer and the sulfidation prevention layer and to prevent the generation of disc defects such as the formation of loose film even after repeated recording or the long-term storage in a severe environment, it is preferable to use a mixture of TiC and TiO. To achieve faster recording speed, larger recording power is required. Therefore, if the adhesion between the sulfidation prevention layer and ZnS—$SiO_2$ or Ag is not strong enough, film peeling-off occurs easily after repeated recording, compared to the optical recording medium for low-speed recording. For SiC, since the coefficients of thermal expansion of Ag and SiC are markedly different from each other, the internal-stress of the film increases upon the initialization or upon recording, and the film peeling-off may occur.

Then, using the mixture of TiO, whose coefficient of thermal expansion is close to that of Ag, and which has good adhesion with Ag, and TiC, which has an effect to prevent the Ag dispersion, for the sulfidation prevention layer between the Ag reflective layer and the second protective layer and combining with the above-mentioned recording layer enable the provision of an optical recording medium where the modulation factor is great, and suitable to high-speed recording, and where the storage stability is more excellent.

Further, setting the total film thickness of the second protective layer and the sulfidation prevention layer at 7 nm to 20 nm enables the provision of the optical recording medium with a greater modulation factor. More preferably, setting the total film thickness of the above-mentioned two layers at 7 nm to 15 nm enables excellent repeated recording characteristics. In high-speed recording, the cooling velocity of the recording layer greatly changes of recording characteristics, so the total film thickness of the second protective layer and the sulfidation prevention layer, which are interposed between the reflective layer and the recording layer greatly affecting the cooling velocity, is important.

It is preferable that the composition of the sulfidation prevention layer be $(TiC)_p(TiO)_{100-p}$ and $50 \leq p \leq 80$ ('p' is % by mass). When 'p' is 80 or less, a greater modulation factor can be obtained, and when 'p' is 50 or greater, excellent repeated recording characteristics can be obtained. The greater 'p' becomes, the greater the thermal conductivity becomes. However, if the thermal conductivity of the sulfidation prevention layer is excessively great, the modulation factor becomes smaller, and if the thermal conductivity is excessively small, heating occurs and the repeated recording characteristic becomes especially poor. The thermal conductivity and the difference of film thickness of the layers interposed between the reflective layer and the recording layer especially affect the high-speed recording, so if these are not within an appropriate range, respectively, excellent recording characteristics where rewritable optical disc system can be realized cannot be obtained.

Further, a layer composed of a mixture of $ZrO_2$, $Y_2O_3$, and $TiO_2$ can be established between the second protective layer and the sulfidation prevention layer with 2 nm to 8 nm of thickness. If using a mixture of TiC and TiO for the sulfidation prevention layer, even though the modulation factor can easily become smaller compared to the case of using SiC, the establishment of the above-mentioned mixture layer increases the modulation factor. For the composition, it is preferable to mix 60 mol % or greater of $ZrO_2$ and 10 mol % or greater of $TiO_2$.

Further, it is preferable to establish an interface layer composed of $SiO_2$ with 2 nm to 4 nm of thickness between the first protective layer and the phase-change recording layer. This reduces damage to a substrate when recording is performed at high power, so the repeated recording characteristic in the high power recording becomes excellent, and the recording power margin can be widened. If the thickness is less than 2 nm, it becomes difficult to form a uniform $SiO_2$ layer, and if the thickness exceeds 4 nm, the recording sensitivity becomes poor and the modulation factor diminishes.

For the transparent substrate, a plastic substrate is generally used. As the plastic substrate, as long as it has transparency and it excels in planar accuracy, there is no special limitation. Any substrate, which has been conventionally used as a transparent substrate for an optical recording medium, can be optionally selected and used. As a typical example, a glass plate and a polycarbonate plate are provided. Concerning the optical constant, it is preferable that the refractive index be 1.5 to 1.6.

In addition, it is preferable that the transparent substrate has a wobbled groove with 0.74±0.03 µm of track pitch, 22 nm to 40 nm of groove depth and 0.2 µm to 0.3 µm of groove width. As a purpose of having the wobbled groove, there are the access to an unrecorded specific track and the rotation of the substrate at a constant linear velocity. The optical recording medium of the present invention is produced for the purpose of enabling response to the recording at approximately 6×-speed to 8×-speed. Sn is added to a GaSb-base material for the purpose of improving the recording characteristic and accelerating the crystallization kinetic. However, it should be noted that the effect of Sn contained in the recording layer causes increased reflectance. For example, as a result of researching about the optical recording medium of the present invention where the groove depth of the transparent substrate is 20 nm, the film thickness of the first protective layer is 30 nm to 100 nm, the film thickness of the recording layer is 5 nm to 50 nm, the film thickness of the second protective layer is 3 nm to 15 nm, the film thickness of the reflective layer is 100 nm to 300 nm and the relative composition ratios of the four elements in the recording layer fulfill the above-mentioned requirement, it has become clear that the reflectance at an unrecorded region (crystalline substance) becomes within the range of 26% to 32%. However, if comparing this reflectance with reflectance at 1×-speed to 4×-speed of DVD+RW, which is a conventional phase-change optical recording medium, it is unnecessarily high. Therefore, taking the compatibility into consideration, it is necessary to adjust the reflectance by reduction.

Therefore, the conditions of the transparent substrate having the wobbled groove with 0.74 f 0.03 µm of track pitch, 22 nm to 40 nm of the groove depth and 0.2 µm to 0.3 µm of groove width are adopted. For example, researching about the transparent substrate by setting the groove depth at 37 nm, the reflectance could be reduced by approximately 2% to 3%. In the DVD disc having track pitch at 0.74±0.03 µm, a push-pull signal is mainly extracted as a signal used for detecting a tracking error. For the push-pull signal, at 660 nm of laser wavelength used for a DVD, the greatest signal intensity can be obtained if using the above-mentioned transparent substrate when the groove depth is 55 nm. In order to adjust the reflectance to be low and to increase the amplitude of an error signal, for the groove depth, the deeper the better. However, also taking the recording characteristic into consideration, it is preferable that the groove depth is within the range of 22 nm to 40 nm. Further, taking the recording characteristic and the signal characteristic into consideration, it has become clear that it is desirable for the groove width to be within 0.2 µm to 0.3 µm.

The present invention can provide a DVD+RW medium that enables the repeated recording at 20 m/s to 28 m/s (approximately 6×-speed to 8×-speed), and where the recording characteristic and storage characteristic are also excellent, and in addition, a DVD+RW where the reflectance of the recording layer is appropriately reduced.

Hereafter, the present invention is more specifically described using Examples and Comparative Examples. However, the present invention will not be limited by these Examples.

Examples A-1 to A-7 and Comparative Examples A-8 to A-19

Discs where the first protective layer ZnS—$SiO_2$ with 60 nm of thickness, the recording layer composed of the phase-change recording material shown in Table 1 with 16 nm of thickness, the second protective layer ZnS—$SiO_2$ with 7 nm of thickness, the sulfidation prevention layer SiC with 4 nm of thickness and the reflective layer Ag with 140 nm of thickness were laminated in this order on a polycarbonate transparent substrate having 0.74 µm of track pitch, 27 nm of groove depth and 0.27 µm of groove width were prepared. These discs were initialized using an initializer for a phase-change disc, and a DVD+RW disc was obtained. For the initialization, an optical head with 48 µm of beam width was used, and crystallization was conducted under the conditions with 1300 mW of power (herein, it is power consumption of LD, and this is different from an irradiation power), 18.5 m/s of scanning speed and 30 µm/rotation of feed.

The recording layers of the above-mentioned discs are all composed of the GaSbSnGe-base material with various optical constants having sufficient transfer linear velocity at 20 m/s or faster. For these discs, the recording linear velocity was set at 6×-speed (20.9 m/s) and 8×-speed (27.9 m/s), and whether or not excellent recording characteristics could be obtained was examined. Recording was performed by repeating the intensity modulation with 2T cycle recording strategy having three levels (Pp>Pe>Pb), peak power 'Pp' for the purpose of forming an amorphous mark, bottom power 'Pb' for the purpose of providing a quenching efficacy and erasure power 'Pe' for the purpose of forming crystalline substance and erasing the information. A pulse generator is DTG-5274 manufactured by Tektronix Japan, Ltd., and the set resolving power is 3.348352 GHz. The evaluation device for this recording is DDU-1000 manufactured by Pulstec Industrial Co., Ltd and the specifications of the recording power are 40 mw with Pp at maximum and 18 mW with Pe at maximum. The peak power Pb was fixed at 0.1 mW and recording was performed. Numerical values used for criteria for the purpose of determining appropriateness of the recording characteristic are "Data to Clock Jitter (hereafter, referred to as DC jitter)" and "modulation factor". The DC jitter is digitization of the gap of ends between the window 'Tw' upon reproducing at 1× speed (corresponding mark length is approximately 0.1333 μm) and nine types of marks regarding the window width Tw as unit (3Tw to 11Tw marks), and it means that the smaller the value becomes, the better the characteristic becomes. The modulation factor indicates how much the difference of the reflectance between a crystalline substance and an amorphous substance is occupied relative to the reflectance of the crystalline substance. Since the greater difference of the crystalline substance can be easily binarized, for the modulation factor, the greater the better. The evaluation criteria are as follows, and the numerical values are values after 10 times of overwriting (DOW10):

<DC jitter> A: 9% or less, B: 11% or less, C: over 11%
<Modulation factor> A: 60% or greater, B: less than 60% evaluated. The bottom jitter after DOW10 at 6×-speed and 8×-speed was 7.9% and 7.7%, respectively; thus excellent characteristics were obtained.

Example A-21

A disc was prepared similarly to Example A-1 except for changing the phase-change recording material to $Ga_5Sb_{70}Sn_{20}Ge_5$ (Sb+Sn=90 atomic %, Nc=2.35, Kc=5.00, Na=4.29, Ka=3.09), and the recording characteristics were evaluated. The bottom jitter after DOW10 at 6×-speed and 8×-speed was 14.5% and 13.7%, respectively.

Example A-22

A disc was prepared similarly to Example A-1 except for changing the phase-change recording material to

TABLE 1

| | | Crystal optical constants at 660 nm | | as-depo optical constants at 660 nm | | transfer linear velocity | recording linear velocity at 20.9 m/s (6× speed) | | recording linear velocity at 27.9 m/s (8× speed) | |
|---|---|---|---|---|---|---|---|---|---|---|
| | Composition of recording layer | Nc | Kc | Na | Ka | (m/s) | Date to clock jitter | Modulation factor | Date to clock jitter | Modulation factor |
| Example 1 | Ga10.5Sb64.5Sn20.0Ge5.0 | 2.59 | 4.31 | 4.31 | 2.96 | 25 | A | A | A | A |
| Example 2 | Ga8.2Sb59.8Sn22.0Ge10.0 | 2.15 | 4.72 | 4.36 | 2.96 | 21 | A | A | C | A |
| Example 3 | Ga5.0Sb70.0Sn17.0Ge8.0 | 2.43 | 4.98 | 4.35 | 2.99 | 27 | A | A | A | A |
| Example 4 | Ga5.0Sb59.0Sn26.0Ge10.0 | 2.14 | 4.68 | 4.26 | 3.05 | 24 | A | A | A | A |
| Example 5 | Ga6.5Sb59.5Sn24.0Ge10.0 | 2.24 | 4.61 | 4.32 | 3.03 | 23 | A | A | B | A |
| Example 6 | Ga5.0Sb60.0Sn25.0Ge10.0 | 2.13 | 4.83 | 4.28 | 3.10 | 24 | A | A | A | A |
| Example 7 | Ga3.0Sb62.0Sn23.0Ge12.0 | 2.18 | 4.80 | 4.32 | 3.08 | 22 | A | A | A | A |
| Comp. Example 8 | Ga3.0Sb76.0Sn14.0Ge7.0 | 3.05 | 4.87 | 4.31 | 3.08 | 34 | A | C | A | C |
| Comp. Example 9 | Ga3.0Sb70.0Sn20.0Ge7.0 | 2.36 | 5.05 | 4.28 | 3.14 | 40 or more | C | C | C | C |
| Comp. Example 10 | Ga3.0Sb68.0Sn22.0Ge7.0 | 2.32 | 5.07 | 4.29 | 3.17 | 40 or more | C | C | C | C |
| Comp. Example 11 | Ga3.0Sb72.0Sn18.0Ge7.0 | 2.38 | 5.08 | 4.30 | 3.12 | 39 | C | C | C | C |
| Comp. Example 12 | Ga5.0Sb70.0Sn20.0Ge5.0 | 2.33 | 5.05 | 4.29 | 3.15 | 40 or more | C | C | C | C |
| Comp. Example 13 | Ga1.0Sb49.0Sn49.0Ge1.0 | 1.60 | 4.80 | | | 40 or more | C | C | C | C |
| Comp. Example 14 | Ga40.0Sb58.0Sn1.0Ge1.0 | 4.25 | 1.42 | 4.37 | 2.00 | 20 | C | C | C | C |
| Comp. Example 15 | Ga13.3Sb81.7Sn5.0 | 3.33 | 4.66 | 4.34 | 2.79 | 20 | C | A | C | A |
| Comp. Example 16 | Ga11.9Sb73.1Sn15.0 | 2.25 | 4.96 | 4.35 | 2.99 | 27 | A | A | A | A |
| Comp. Example 17 | Ga11.2Sb68.8Sn20.0 | 2.10 | 4.68 | 4.30 | 3.14 | 38 | A | C | A | C |
| Comp. Example 18 | Ga12.6Sb77.4Sn0.0 | 2.64 | 4.86 | 4.34 | 2.92 | 23 | A | A | B | A |
| Comp. Example 19 | Ga13.6Sb71.4Sn15.0 | 2.38 | 4.85 | 4.34 | 2.95 | 24 | A | A | B | A |
| Example 22 | Ga11Sb64Sn20Ge5 | 2.61 | 4.32 | 4.3 | 3.05 | 28 | A | A | A | A |
| Example 23 | Ga6Sb66Sn22Ge6 | 2.3 | 4.81 | 4.31 | 2.87 | 30 | A | A | A | A |

<Comparison of Recording Characteristic Regarding Total Composition Ratio (Atomic %) of Sb to Sn>

With respect to discs in Example A-2 and the below-mentioned Examples A-20 to A-23, the recording characteristics were compared.

Figure 4:
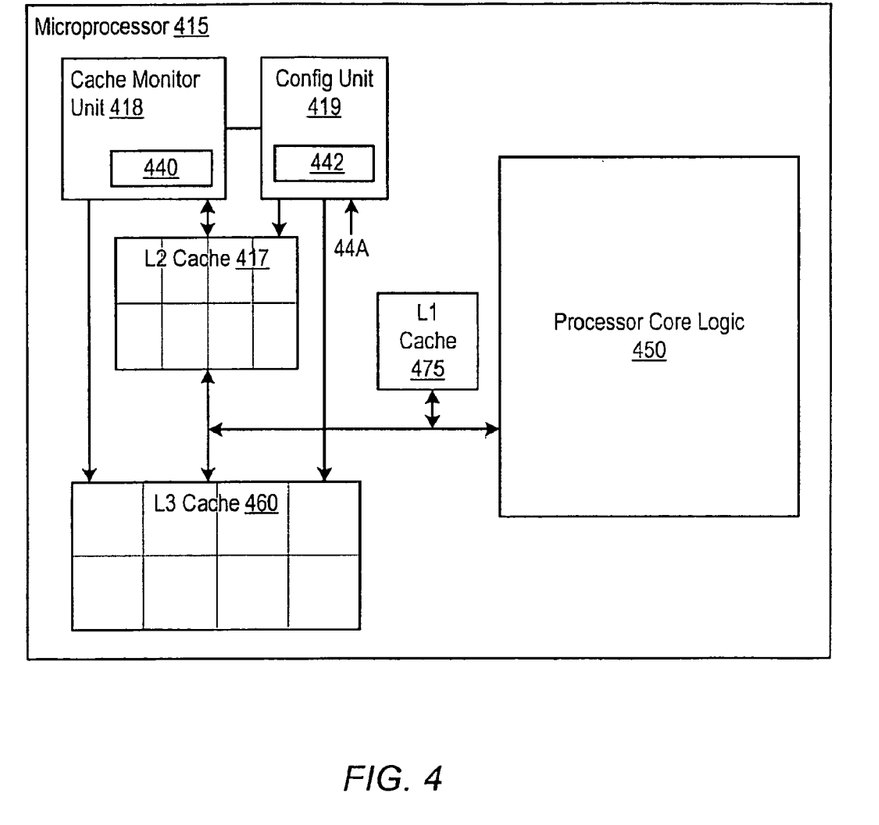
FIG. 4 is a comparison chart of recording characteristic regarding the total composition ratio (atomic %) of Sb to Sn in Examples A-2, A-20 and A-21.

For the discs in Examples A-2, A-20 and A-21, FIG. 4 shows the compared result of the DC jitter after DOW10 at 8×-speed in the case of changing the peak power (Example A-2: the line through the triangular points, Example A-20: the line through the diamond points, and Example A-21: the line through the rectangular points), and Table 1 shows the result in Examples A-22 and A-23.

The recording characteristic of the disc in Example A-2 (Sb+Sn=81.8 atomic %) was evaluated, and the bottom jitter after DOW10 at 6×-speed and 8×-speed was 8.9% and 13.9%, respectively.

Example A-20

A disc was prepared similarly to Example A-1 except for changing the phase-change recording material to $Ga_7Sb_{69}Sn_{18}Ge_6$ (Sb+Sn=87 atomic %, Nc=2.25, Kc=4.90, Na=4.30, Ka=3.01), and the recording characteristics were $Ga_{11}Sb_{64}Sn_{20}Ge_5$ (Sb+Sn=84 atomic %, Nc=2.61, Kc=4.32, Na=4.30, Ka=3.05), and the recording characteristics were evaluated. The bottom jitter after DOW10 at 6×-speed and 8×-speed was 8.5% and 8.9%, respectively; thus excellent characteristics were obtained.

Example A-23

A disc was prepared similarly to Example A-1 except for changing the phase-change recording material to $Ga_6Sb_{66}Sn_{22}Ge_6$ (Sb+Sn=88 atomic %, Nc=2.30, Kc=4.81, Na=4.31, Ka=2.87), and the recording characteristics were evaluated. The bottom jitter after DOW10 at 6×-speed and 8×-speed was 8.2% and 8.8%, respectively; thus excellent characteristics were obtained.

<Comparison of Jitter, Modulation Factor and Reflectance According to Groove Depth>

Figure 5:
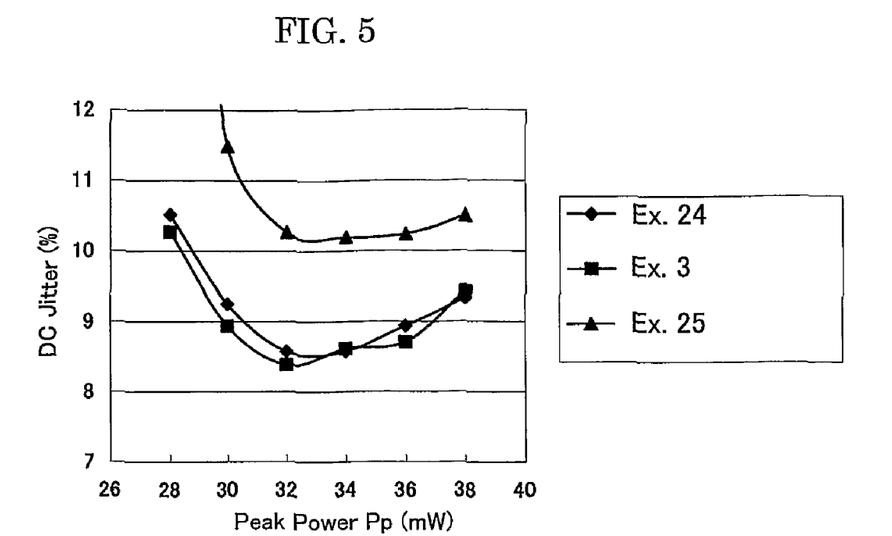
FIG. 5 is a chart showing the comparison result of DC jitter in Examples A-3, A-24 and A-25.
Figure 6:
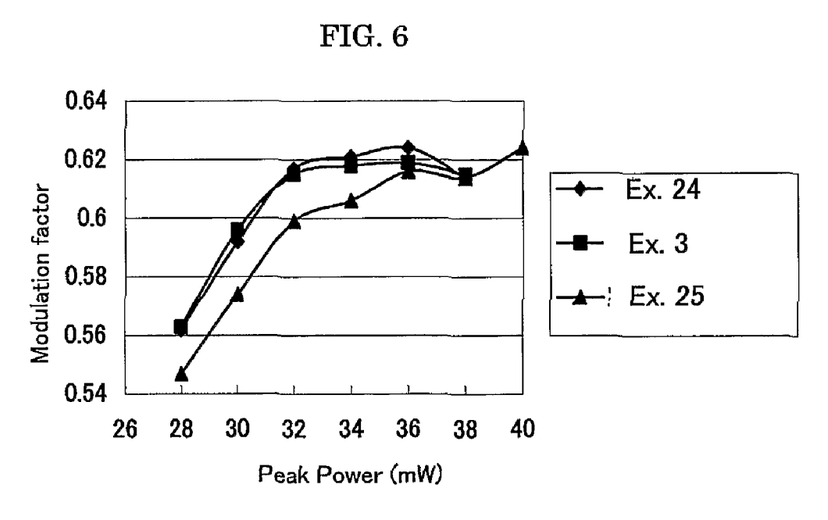
FIG. 6 is a chart showing the comparison result of modulation factor in Examples A-3, A-24 and A-25.

With respect to each disc in Examples A-3, A-24 and A-25, FIG. 5 to FIG. 7 show the comparison results of the DC jitter, the modulation factor and the reflectance in the case of changing the peak power (Example A-3 (groove depth: 27 nm): the line through the rectangular points, Example A-24 (groove depth: 37 nm): the line through the diamond points, Example A-25 (groove depth: 42 nm): the line through the triangular points), respectively.

The bottom jitter of the disc in Example A-3 after DOW10 at 6x-speed and 8x-speed shown in Table 1 was 8.0% and $Ga_3Sb_{67}Sn_{14}Ge_8Te_8$, and the recording characteristics were evaluated. The result is shown in Table 2.

TABLE 2

| | Crystal optical constants | | as-depo optical constants | | Composition of recording layer | | | | | transfer linear velocity | recording linear velocity at 20.9 m/s | | recording linear velocity at 27.9 m/s | |
|---|---|---|---|---|---|---|---|---|---|---|---|---|---|---|
| | Nc | Kc | Na | Ka | Ga | Sb | Sn | Ge | Te | (m/s) | Date to clock | modulation factor | Date to clock | modulation factor |
| Example 26 | 2.51 | 4.7 | 4.32 | 2.94 | 7 | 68 | 15 | 6 | 4 | 24 | 8.3 (A) | 62 (A) | 8.5 (A) | 61 (A) |
| Example 27 | 2.96 | 4.71 | 4.24 | 2.94 | 5 | 68 | 15 | 7 | 5 | 25 | 8.3 (A) | 61 (A) | 8.1 (A) | 60 (A) |
| Comp. Example 28 | 3.08 | 4.81 | 4.3 | 2.99 | 3 | 68 | 15 | 8 | 6 | 27 | 9.1 (B) | 60 (A) | 9.1 (B) | 56 (B) |
| Comp. Example 29 | 3.17 | 4.71 | 4.29 | 2.88 | 3 | 67 | 14 | 8 | 8 | 23.5 | 11.2 (C) | 60 (A) | 12.4 (C) | 56 (B) |

8.4%, respectively, and the modulation factor was also excellent, which was 61.5%, and the reflectance at an unrecorded region (R14H) at that time was 26.5%.

Example A-24

A disc was prepared similarly to Example A-3 except for changing the groove depth of the substrate to 37 nm, and the recording characteristics were evaluated. The bottom jitter after DOW10 at 6x-speed and 8x-speed was 8.2% and 8.6%, respectively, and the modulation factor was excellent, which was 61.7%, and the reflectance at an unrecorded region (R14H) at that time was 24.4%.

Example A-25

A disc was prepared similarly to Example A-3 except for changing the groove depth of the substrate to 42 nm, and the recording characteristics were evaluated. The bottom jitter after DOW10 at 6x-speed and 8x-speed was 9.7% and 10.2%, respectively, so both showed slight deterioration, and the modulation factor was 61.6% and the reflectance at an unrecorded region (R14H) at that time was 22.1%. Although lower reflectance could be obtained, the recording characteristics had slightly deteriorated.

Example A-26

A disc was prepared similarly to Example A-1 except for changing the phase-change recording material to $Ga_7Sb_{68}Sn_{15}Ge_6Te_4$, and the recording characteristics were evaluated. The result is shown in Table 2.

Example A-27

A disc was prepared similarly to Example A-1 except for changing the phase-change recording material to $Ga_5Sb_{68}Sn_{15}Ge_7Te_5$, and the recording characteristics were evaluated. The result is shown in Table 2.

Example A-28

A disc was prepared similarly to Example A-1 except for changing the phase-change recording material to $Ga_3Sb_{68}Sn_{15}Ge_8Te_6$, and the recording characteristics were evaluated. The result is shown in Table 2.

Example A-29

A disc was prepared similarly to Example A-1 except for changing the phase-change recording material to As it is clear from the above-mentioned Table 2, Nc exceeded 3.0 in Comparative Examples A-28 and A-29, and preferable results could not be obtained for both the jitter and the modulation factor.

According to the above-mentioned Examples and Comparative Examples, it has been demonstrated that using the GaSbSnGe-base phase-change recording layer material having optical constants provided in the present invention enables recording at 6x-speed to 8x-speed of recording linear velocity. Further, according to Examples A-2 and A-20 to A-23, it is clear that if the total composition ratio of Sb to Sn is within the range of $84 \leq \beta + \gamma \leq 88$, further excellent recording characteristic and storage stability can be obtained.

Further, according to Examples A-3, A-24 and A-25, in the case that the transparent substrate has a wobbled groove with $0.74 \pm 0.03$ μm of track pitch, 22 nm to 40 nm of groove depth and 0.2 μm to 0.3 μm of groove width, it is clear that while excellent recording characteristics are maintained, the reflectance can be controlled to be low.

Examples B-1 to B-7

The first protective layer, the phase-change recording layer, the second protective layer, the sulfidation prevention layer and the reflective layer were deposited in order onto a polycarbonate substrate with 0.74 μm of track pitch, 27 nm of groove depth, 12 cm of diameter and 0.6 mm of thickness according to the sputtering method.

For the first protective layer, $(ZnS)_{80}(SiO_2)_{20}$ (mol %) was used as a target and the film thickness was set at 60 nm.

For the phase-change recording layer, $Sn_{18}Sb_{68}Ga_5Ge_9$ (atomic %), Nc=2.33, Kc=4.88, Na=4.45, Ka=2.89, was used as a target and the film thickness was set at 16 nm.

For the second protective layer, $(ZnS)_{80}(SiO_2)_{20}$ (mol %) was used as a target and the film thickness was set as shown in Table 3.

For the sulfidation prevention layer, $(TiC)_{70}(TiO)_{30}$ (mass %) was used as a target and the film thickness was set as shown in Table 3.

For the reflective layer, Ag was used as a target and the film thickness was set at 180 nm.

Subsequently, after applying acrylic-base cured resin (SD318 manufactured by Dainippon Ink and Chemicals, Incorporated) with 8 μm of thickness onto the reflective layer according to the spin coating method, the film was cured by ultraviolet ray in an $N_2$ atmosphere and a resin protective layer was formed.

In addition, another polycarbonate substrate with 12 cm of diameter and 0.6 mm of thickness was bonded onto the resin protective layer using an adhesive, and a disc-shaped optical recording medium was obtained.

Subsequently, the optical recording medium was initialized using an initializer (POP120-7AH manufactured by Hitachi Computer Peripherals Co., Ltd.) having a laser head where a focusing function was added to a laser beam with 830 nm of output wavelength, approximately 1 μm of width, 75 μm of length and 2 W of maximum output. Fixed initialization conditions were 1500 mW of laser output, 20 m/s of scanning speed and 50 μm of head feed.

TABLE 3

|  | Second protective layer (nm) | sulfidation prevention layer (nm) |
|---|---|---|
| Example 1 | 2 | 3 |
| Example 2 | 4 | 3 |
| Example 3 | 7 | 4 |
| Example 4 | 11 | 4 |
| Example 5 | 13 | 4 |
| Example 6 | 10 | 10 |
| Example 7 | 15 | 7 |

With respect to the optical recording media prepared as mentioned above, recording and reproducing were evaluated using the optical disc evaluating device (DDU-1000 manufactured by Pulstec Industrial Co., Ltd) having a pickup with 650 nm of wavelength and 0.65 of NA. The recording linear velocity was set at 28 m/s (equivalent to 8×-speed of DVD), the jitter (data to clock jitter: a value where 'σ' is standardized with detection window width 'Tw') when repeatedly recording the random pattern 10 times with EFM+modulation method and the modulation factor are shown in Table 4. The recording strategy was optimized, and reproducing was all performed at 3.5 m/s of linear velocity with 0.7 mW of power.

TABLE 4

|  | DOW10 modulation factor | DOW10 jitter (%) |
|---|---|---|
| Example 1 | 52 | 12.1 |
| Example 2 | 62 | 8.5 |
| Example 3 | 67 | 8.3 |
| Example 4 | 71 | 8.9 |
| Example 5 | 70 | 11.2 |
| Example 6 | 62 | 11.5 |
| Example 7 | 52 | 13.2 |

As it is clear from Table 4, in the case that the total film thickness of the first protective layer and the sulfidation prevention layer is especially 7 nm to 20 nm, 60% or greater modulation factor, which is a standard value for DVD-ROM, could be obtained. In addition, in the case that the total film thickness is 7 nm to 15 nm, the jitter after 10 times of repeated recording was within 9%, which is a standard value; thus preferable repeated recording characteristics could be obtained. In the case that the total film thickness was less than 7 nm, the modulation factor was small and the jitter was 9% or greater. This was because heat was not sufficiently applied to the recording layer, the fused region was narrow, and the formed mark was small. Further, in the case that the total film thickness exceeded 20 nm, the modulation factor was also small and the jitter was also 9% or greater, because even though the fused region was wide, the period of time to be maintained in the temperature range where re-crystallization occurs was long, so re-crystallization progressed from the periphery of the mark, and as a result, the formed mark became small.

In addition, after storing each of the above-mentioned optical recording media for 100 hours in an environment of 80° and 85% RH, the optical recording media were visually observed by holding each of them to a lamp, and no pinhole generation was confirmed in any of them.

Furthermore, the transfer linear velocity of the recording medium in Example B-1 was 28 m/s.

Examples B-8 to B-12

Disc-shaped optical recording media were prepared similarly to Example 1 except for changing the phase-change recording material to $Sn_{13}Sb_{72}Ga_7Ge_8$, Nc=2.21, Kc=4.97, Na=4.36, Ka=2.98, setting the film thickness of the first protective layer at 8 nm and the film thickness of the sulfidation prevention layer at 5 nm, and changing the composition of the sulfidation prevention layer to that shown in Table 5.

With respect to these optical recording media, recording and reproducing were evaluated using the optical evaluating device (DDU-1000 manufactured by Pulstec Industrial Co., Ltd) having a pickup with 650 nm of wavelength and 0.65 of NA. The recording linear velocity was set at 28 m/s (equivalent to 8×-speed of DVD), and the modulation factor upon repeatedly recording a random pattern 10 times with EFM+ modulation method and the jitter upon repeatedly recording 1,000 times were examined. If the jitter was greater than 9%, the optical recording medium was graded as B, and if the jitter is 9% or less, the medium was graded A, and the result is shown in Table 5.

As it is clear from Table 5, in the case that TiC was 80 (% by mass) or less, the modulation factor after DOW10 was 60% or greater. Further, in the case that TiC was 40 (% by mass), the modulation factor was greater, but the jitter after DOW1000 was 9% or greater.

Furthermore, the transfer linear velocity of the recording medium in Example B-8 was 29 m/s.

TABLE 5

|  | TiC (mass %) | TiO (mass %) | DOW10 modulation factor | DOW1000 characteristics |
|---|---|---|---|---|
| Example 8 | 40 | 60 | 68 | B |
| Example 9 | 50 | 50 | 67 | A |
| Example 10 | 70 | 30 | 65 | A |
| Example 11 | 80 | 20 | 61 | A |
| Example 12 | 90 | 10 | 55 | A |

Example B-13

Disc-shaped optical recording media were prepared similarly to Example B-3 except for changing the phase-change recording material to $Sn_{20}Sb_{65}Ga_5Ge_{10}$ (Nc=2.43, Kc=4.80, Na=4.40, Ka=2.78 and the transfer linear velocity=26 m/s).

With respect to this optical recording medium, recording and reproducing were evaluated using the optical disc evaluating device (DDU-1000 manufactured by Pulstec Industrial Co., Ltd) having a pickup with 650 nm of wavelength and 0.65 of NA. The recording linear velocity was set at 28 m/s (equivalent to 8×-speed of DVD), and it was optimized with 32 mW of recording power Pw, 0.1 mW of bottom power Pb, and 5 mW to 10 mW of erasing power Pe. A random pattern was repeatedly recorded with EFM+modulation method and the jitter (data to clock jitter: a value where 'σ' was standardization with detection window width 'Tw') was evaluated.

The recording strategy was optimized, and reproducing was all performed at 3.5 m/s of linear velocity with 0.7 mW of power.

In addition, after this optical recording medium was stored for 100 hours in an environment of 80° C. and 85% RH, recording was performed under the same condition. Each result is shown in FIG. 9 (before the storage test: the line through the rectangular points, after storage test: the line through the diamond points).

Figure 9:
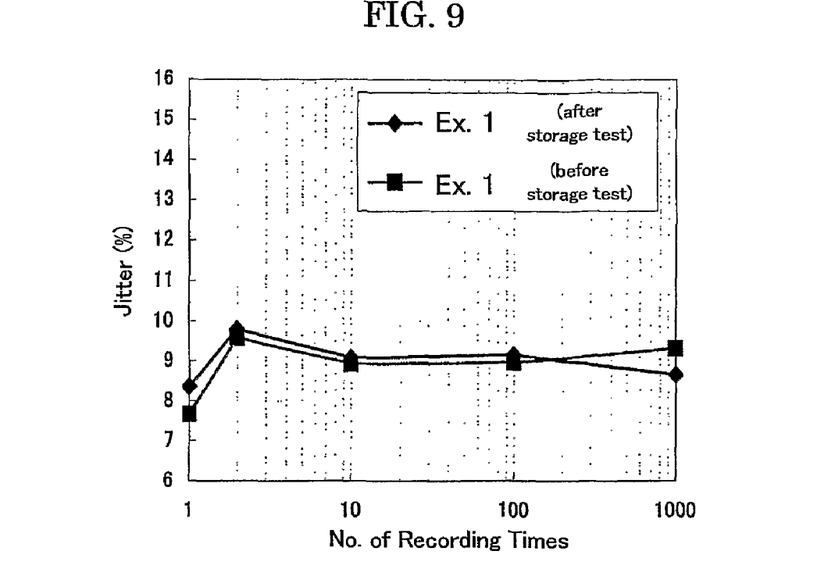
FIG. 9 is a chart showing the evaluation result of the optical recording medium in Example B-1.

As it is clear from FIG. 9, even after 100-hour storage in an environment of 80° and 85% RH, no great jitter deterioration was confirmed. The optical recording medium after this storage test was visually observed by holding it to a lamp; however, no pinhole generation was confirmed.

Example B-14

A disc-shaped optical recording medium was prepared similarly to Example B-13 except for changing the phase-change recording material to $Sn_{20}Sb_{65}Ga_3Ge_7Te_5$ (atomic %), Nc=2.50, Kc=4.80, Na=4.35, Ka=2.68, the transfer linear velocity=24 m/s, and changing the film thickness of the second protective layer to 10 nm. Recording was performed similarly to Example B-13, and the jitter after DOW1 was improved more than that in Example B-13. It is considered that because the addition of Te resulted in the uniform initial crystallization, the jitter rise after DOW1 was diminished.

In addition, after this optical recording medium was stored for 100 hours in an environment of 80° C. and 85% RH, recording was performed under the same condition. Each result is shown in FIG. 10 (before the storage test: the line through the rectangular points, after storage test: the line through the diamond points).

Figure 10:
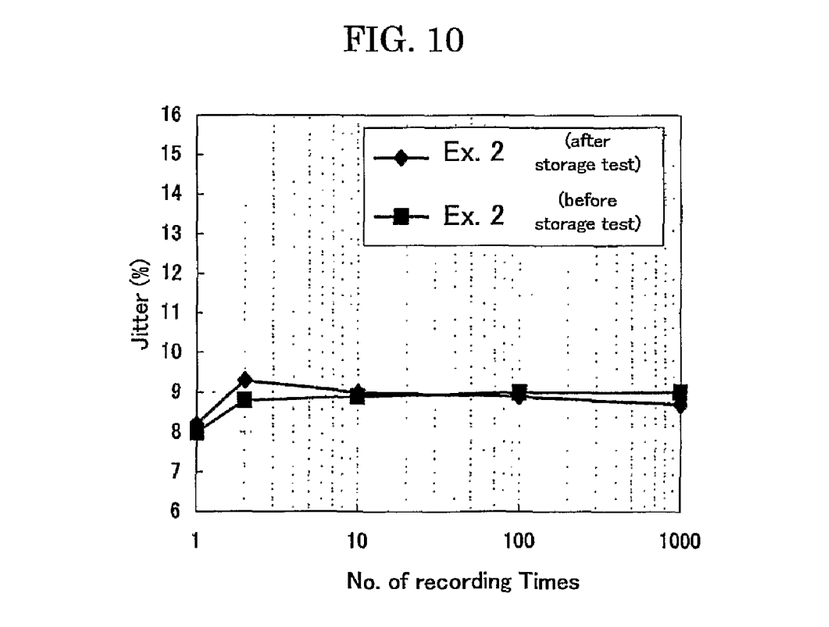
FIG. 10 is a chart showing the evaluation result of the optical recording medium in Example B-2.

As it is clear from FIG. 10, even after 100-hour storage in an environment of 80° C. and 85% RH, no great jitter deterioration was confirmed. The optical recording medium after this storage test was visually observed by holding it to a lamp; however, no pinhole generation was confirmed.

Example B-15

An optical recording medium was prepared under similar conditions to those in Example B-13 except for changing the phase-change recording material to $Sn_{16}Sb_{70}Ga_6Ge_8$ (atomic %) (Nc=2.43, Kc=4.90, Na=4.36 and Ka=2.97, and the transfer linear velocity=27 m/s), changing the film thickness of the second protective layer to 5 nm, targeting $(TiC)_{60}(TiO)_{40}$ (% by mass) for the sulfidation prevention layer, and changing its film thickness to 3 nm. Recording was performed similarly to Example B-13, and the jitter decreased by 0.5% compared to that in Examples B-13.

In addition, after this optical recording medium was stored for 100 hours in an environment of 80° C. and 85% RH, recording was performed under the same condition. No great jitter deterioration was confirmed. The optical recording medium after this storage test was visually observed by holding it to a lamp; however, no pinhole generation was confirmed.

Example B-16

An optical recording medium was prepared under similar conditions to those in Example B-13 except for changing the film thickness of the first protective layer to 70 nm, changing the phase-change recording material to $Sn_{19}Sb_{63}Ga_9Ge_9$ (atomic %) (Nc=2.21, Kc=4.61, Na=4.31, Ka=2.88, and the transfer linear velocity=22 m/s), changing its film thickness to 14 nm, changing the film thickness of the second protective layer to 4 nm, targeting $(TiC)_{50}(TiO)_{50}$ (% by mass) for the sulfidation prevention layer, and establishing a layer containing a mixture of $ZrO_2$, $Y_2O_3$, and $TiO_2$ with 3 nm of film thickness between the second protective layer and the sulfidation prevention layer. Recording was performed similarly to Example B-13, and the jitter characteristic, which was the same level as that in Example 13, was obtained, and the modulation factor increased by 2%.

In addition, after this optical recording medium was stored for 100 hours in an environment of 80° C. and 85% RH, recording was performed under the same condition. No great jitter deterioration was confirmed. The optical recording medium after this storage test was visually observed by holding it to a lamp; however, no pinhole generation was confirmed.

Example B-17

An Optical Recording Medium was Prepared Under Similar conditions to those in Example B-13 except for changing the film thickness of the first protective layer to 58 nm, establishing an $SiO_2$ layer with 2 nm of film thickness between the first protective layer and the phase-change recording layer, changing the phase-change recording material to $Sn_{14}Sb_{68}Ga_{10}Ge_8$ (atomic %) (Nc=2.38, Kc=4.87, Na=4.38, Ka=2.55, and the transfer linear velocity=24 m/s), changing its film thickness to 14 nm, changing the film thickness of the second protective layer to 4 nm, and changing the film thickness of the sulfidation prevention layer to 6 nm. Recording was performed similarly to Example B-13, and the repeated recording characteristic upon recording with higher power than that of Example B-13 was improved.

In addition, after this optical recording medium was stored for 100 hours in an environment of 80° C. and 85% RH, recording was performed under the same condition. No great jitter deterioration was confirmed. The optical recording medium after this storage test was visually observed by holding it to a lamp; however, no pinhole generation was confirmed.

Example B-18

An Optical Recording Medium was Prepared Under Similar conditions to those in Example B-13 except for changing the film thickness of the second protective layer to 10 nm and changing the sulfidation prevention layer material to SiC. Recording was performed similarly to Example B-13, and the jitter characteristic, which was the same level as that in Example B-13, was obtained. However, after this optical recording medium was stored for 100 hours in an environment of 80° C. and 85% RH, recording was performed under the same conditions, and when the optical recording medium after this storage test was held to a lamp, pinholes were visually observed. Furthermore, the transfer linear velocity of the recording medium in Example B-18 was 26 m/s, Nc=2.37, Kc=4.82, Na=4.45, and Ka=2.88).

Comparative Example B-1

An optical recording medium was prepared under similar conditions to those in Example B-13 except for changing the phase-change recording material to $Ag_5In_5Sb_{65}Te_{25}$ (atomic %) and changing the film thickness of the second protective layer to 10 nm. Recording was performed similarly to Example B-13; however, recording could not be repeatedly performed. The optical recording medium after this storage test was visually observed by holding it to a lamp, and no pinhole generation was confirmed.

The invention claimed is:

1. An optical recording medium comprising:
   a transparent substrate,
   a first protective layer disposed on the transparent substrate,
   a recording layer disposed on the first protective layer,
   a second protective layer disposed on the recording layer, and
   a reflective layer disposed on the second protective layer,
   wherein the recording layer is composed of a phase-change recording material comprising Ga, Sb, Sn and Ge, and where the transfer linear velocity is 20 m/s to 30 m/s,
   wherein when the wavelength of a recording and reproducing light is within the range of 650 nm to 665 nm and the recording linear velocity is 20 m/s to 28 m/s, the refractive index Nc and the extinction coefficient Kc in a crystalline state and the refractive index Na and the extinction coefficient Ka in an amorphous state in the recording layer respectively satisfy the following numerical expressions:

$2.0 \leq Nc \leq 3.0$, $4.0 \leq Kc \leq 5.0$, $4.0 \leq Na \leq 5.0$, and $2.5 \leq Ka \leq 3.1$, and wherein information is recordable at the range of 20 m/s to 28 m/s of recording linear velocity,
   wherein the optical recording medium further comprises a sulfidation prevention layer between the second protective layer and the reflective layer, and
   wherein the optical recording medium further comprises an additional layer containing a mixture of $ZrO_2$, $Y_2O_3$, and $TiO_2$ with 2 nm to 8 nm of film thickness between the second protective layer and the sulfidation prevention layer.

2. The optical recording medium according to claim 1, wherein when the mutual composition ratios (atomic %) of the four elements, Ga, Sb, Sn and Ge, in the recording layer are regarded as $\alpha$, $\beta$, $\gamma$ and $\delta$, respectively, these satisfy the following numerical expressions:

$2 \leq \alpha \leq 11$, $59 \leq \beta \leq 70$, $17 \leq \gamma \leq 26$, $2 \leq \delta \leq 12$, $84 \leq \beta + \gamma \leq 88$, and $\alpha + \beta + \gamma + \delta = 100$.

3. The optical recording medium according to claim 1, wherein the total of contents of the four elements, Ga, Sb, Sn and Ge, in the recording layer is 95 atomic % or greater relative to all elements in the recording layer.

4. The optical recording medium according to claim 3, wherein the recording layer further comprises Te.

5. The optical recording medium according to claim 1, wherein the film thickness of the first protective layer is 30 nm to 100 nm, the film thickness of the recording layer is 5 nm to 50 nm, the film thickness of the second protective layer is 3 nm to 15 nm and the film thickness of the reflective layer is 100 nm to 300 nm.

6. The optical recording medium according to claim 1, wherein the transparent substrate has a wobbled groove with 0.74±0.03 μm of track pitch, 22 nm to 40 nm of groove depth and 0.2 μm to 0.3 μm of groove width.

7. An optical recording medium comprising:
   a transparent substrate,
   a first protective layer disposed on the transparent substrate,
   a recording layer disposed on the first protective layer,
   a second protective layer disposed on the recording layer, and
   a reflective layer disposed on the second protective layer,
   wherein the recording layer is composed of a phase-change recording material comprising Ga, Sb, Sn and Ge, and where the transfer linear velocity is 20 m/s to 30 m/s,
   wherein when the wavelength of a recording and reproducing light is within the range of 650 nm to 665 nm and the recording linear velocity is 20 m/s to 28 m/s, the refractive index Nc and the extinction coefficient Kc in a crystalline state and the refractive index Na and the extinction coefficient Ka in an amorphous state in the recording layer respectively satisfy the following numerical expressions:

$2.0 \leq Nc \leq 3.0$, $4.0 \leq Kc \leq 5.0$, $4.0 \leq Na \leq 5.0$, and $2.5 \leq Ka \leq 3.1$, and wherein information is recordable at the range of 20 m/s to 28 m/s of recording linear velocity,
   wherein the optical recording medium further comprises a sulfidation prevention layer between the second protective layer and the reflective layer, and
   wherein the first protective layer and the second protective layer comprises a mixture of ZnS and $SiO_2$, respectively, the sulfidation prevention layer comprises a mixture of TiC and TiO, and the reflective layer comprises Ag or an alloy where Ag is a main component,
   wherein the optical recording medium further comprises an additional layer containing a mixture of $ZrO_2$, $Y_2O_3$, and $TiO_2$ with 2 nm to 8 nm of film thickness between the second protective layer and the sulfidation prevention layer.

8. The optical recording medium according to claim 7, wherein the total film thickness of the second protective layer and the sulfidation prevention layer is 7 nm to 20 nm.

9. The optical recording medium according to claim 8, wherein the total film thickness of the second protective layer and the sulfidation prevention layer is 7 nm to 15 nm.

10. The optical recording medium according to claim 7, wherein the composition of the sulfidation prevention layer is $(TiC)_p(TiO)_{100-p}$, wherein 'p' represent percentage by mass and satisfy the following numerical expressions, $50 \leq p \leq 80$.

11. The optical recording medium according to claim 7, wherein the optical recording medium further comprises a layer containing $SiO_2$ with 2 nm to 4 nm of film thickness between the first protective layer and the phase-change recording layer.

12. The optical recording medium according to claim 1, wherein the additional layer includes 60 mol % or greater of $ZrO_2$ and 10 mol % or greater of $TiO_2$.

13. The optical recording medium according to claim 1, wherein the additional layer is configured to increase a modulation factor of the optical recording medium.

* * * * *